United States Patent [19]
Chang

[11] Patent Number: 5,779,624
[45] Date of Patent: Jul. 14, 1998

[54] SIGMOID SPLINT DEVICE FOR ENDOSCOPY

[75] Inventor: Stanley F. Chang, Fresno, Calif.

[73] Assignee: Boston Scientific Corporation, Natick, Mass.

[21] Appl. No.: 760,704

[22] Filed: Dec. 5, 1996

[51] Int. Cl.$^6$ .................................................. A61B 1/04
[52] U.S. Cl. ........................ 600/114; 600/201; 600/235; 604/167
[58] Field of Search ..................... 600/114, 139, 600/129, 138, 153, 156, 201, 208, 210, 235, 144, 184; 604/27, 48, 54, 73, 93, 160, 167, 239, 264, 278, 285, 256, 321, 336

[56] References Cited

U.S. PATENT DOCUMENTS

| | | |
|---|---|---|
| 3,417,746 | 12/1968 | Moore . |
| 3,805,770 | 4/1974 | Okada ........................... 600/114 |
| 3,822,697 | 7/1974 | Komiya .......................... 600/114 |
| 3,860,006 | 1/1975 | Patel . |
| 4,353,358 | 10/1982 | Emerson . |
| 4,577,621 | 3/1986 | Patel ............................. 600/114 |
| 4,601,283 | 7/1986 | Chikama . |
| 4,646,722 | 3/1987 | Silverstein . |
| 4,696,544 | 9/1987 | Costella ....................... 600/114 X |
| 4,765,314 | 8/1988 | Kolditz et al. ................ 600/114 |
| 5,109,830 | 5/1992 | Cho . |
| 5,217,001 | 6/1993 | Nakao et al. .................. 128/4 |
| 5,280,781 | 1/1994 | Oku ............................. 600/114 |
| 5,337,733 | 8/1994 | Bauerfeind et al. .......... 600/114 X |
| 5,370,109 | 12/1994 | Cuny . |
| 5,386,818 | 2/1995 | Schneebaum . |
| 5,391,155 | 2/1995 | Sachse . |
| 5,409,468 | 4/1995 | Sachse . |
| 5,411,483 | 5/1995 | Loomas et al. ............... 604/167 |
| 5,429,609 | 7/1995 | Yoon ........................... 604/167 |
| 5,628,732 | 5/1997 | Antoon, Jr. et al. .......... 605/256 X |

OTHER PUBLICATIONS

Hiromi Shimya, Splinting Device (sliding tube), "Colonoscopy: Diagnosis and Treatment of Colonic Diseases," 1982 pp. 69–76, pub.: Igku–Shoin.

Primary Examiner—Beverly M. Flanagan
Attorney, Agent, or Firm—Richard A. Ryan

[57] ABSTRACT

Disclosed is a splint or overtube device for use in keeping the sigmoid colon in a straightened position during endoscopy to facilitate advancement of the colonoscope or other types of medical endoscopes to the cecum. This device utilizes a distal seal made from a sponge-like material to close off the space between the endoscope and the splint at the distal end of the splint to prevent perforation of the colon. The distal seal can be tapered to further facilitate passage of the splint through the colon and minimize the likelihood of colon perforations. A hydrophilic lubricating substance is utilized to minimize friction between the endoscope and the splint. A second sealing member is utilized at the proximal end of the splint to prevent loss of fluids from the splint and to guide the endoscope through the splint. An injection port is provided to allow the endoscope operator to inject fluid to lubricate the distal seal, to enlarge the colon in advance of the splint and to clear a path through the colon for the splint.

26 Claims, 7 Drawing Sheets

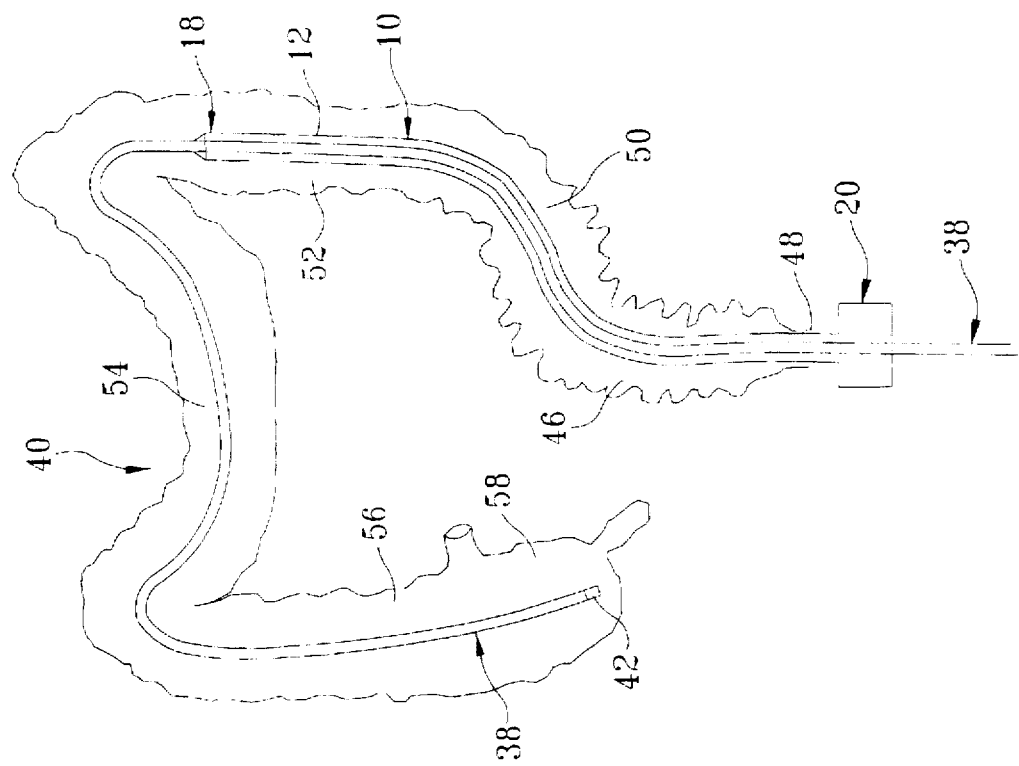
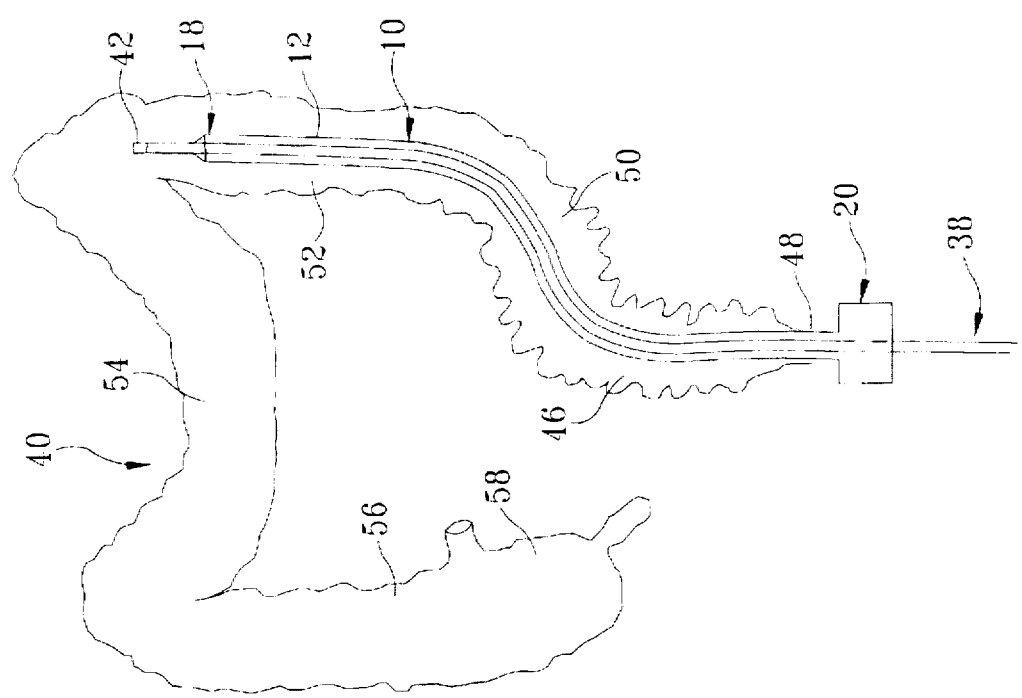
FIG. 5D
FIG. 5C

SIGMOID SPLINT DEVICE FOR ENDOSCOPY

BACKGROUND OF THE INVENTION

1. Field of the Invention

The field of the present invention relates generally to devices for use in endoscopic examinations of the human colon. More specifically, the device described herein relates to medical equipment to facilitate the insertion of an endoscope into the human colon by keeping the sigmoid colon in a straightened position. Even more specifically, this device relates to splints or overtubes used over and in conjunction with an endoscope to straighten the sigmoid colon for the purpose of facilitating the insertion and movement of the endoscope through the sigmoid colon.

2. Background

As used herein, the term "splint" is used interchangeably with the term "overtube" to generally describe the device that is the subject of this patent. The term "endoscope" or "scope" is used to refer to a colonoscope, gastroscope, enteroscope, or other types of medical endoscopes. In referring to the opposite ends of the splint or scope, the "proximal end" means that part of the splint or scope which is closest to the operator or physician/surgeon performing the endoscopy and the "distal end" means that part of the splint or scope farthest from the operator or physician/surgeon.

Colonoscopy is the most sensitive and specific means for examining the colon, particularly for the diagnosis of colon cancers and polyps. Because the cecum, the portion of the colon furthest from the anus, is a common location for cancer, it is important that the entire colon be completely examined. In addition, Western countries have experienced a "rightward shift" of cancers of the colon in recent years as cancers of the right colon have become more common. However, because the anatomy of the colon can extremely vary from person to person, the technique of total colonoscopy is technically demanding.

During an endoscopy, the scope is inserted in the anus, through the rectum, sigmoid colon, descending colon, transverse colon, ascending colon and then into the cecum. Advancing the scope, which is typically about 160 centimeters in length, can be difficult due to a loop in the sigmoid colon. Once the scope reaches the descending colon or transverse colon, this loop must be reduced by withdrawing the scope to a straightened position. Failure to straighten the loop in the sigmoid colon prior to continuing can cause enlargement of the loop and result in pain and damage, including adverse cardiac reactions such as hypotension and bradycardia. Once the loop is straightened, further advancement of the endoscope can usually be accomplished.

In patients having long sigmoid colons, reaching the cecum may be extremely difficult, if not impossible, due to reformation of the sigmoid loop when the operator attempts further advancement of the scope. Continued pushing of the scope under these circumstances enlarges the loop, rather than advancing the tip of the scope. Scope operators often employ various maneuvers to complete the examination, including changing the patient's position and the use of abdominal compressions. Unfortunately, these maneuvers prolong the procedure and are not always successful in helping the scope reach the cecum. Even expert colonoscopists experience difficulties in 10-20% of cases because of the long sigmoid colon problem. The overall success rate for total colonoscopy, i.e. getting the tip of the colonoscope to the cecum, has been reported to be 55-98%.

3. Prior Art

The existing sigmoid splint has been in existence for over twenty years. When used correctly, it has proven to be a very helpful tool by allowing successful examination to the cecum, speeding up the procedure and making it less painful to the patient. The prior art splint is a hollow cylinder about 40 centimeters in length. It is made of a flexible but slightly rigid material, such as plastic, polyethylene, polyurethane, vinyl, or polyvinyl, of about 1 millimeter in thickness. The distal end of the prior art splint is tapered to an inner diameter about 4 millimeter greater than the scope. Its proximal end is much larger in diameter in order to prevent entry into the patient's body and has a rubber diaphragm with a hole slightly larger in diameter than the outside diameter of the scope to allow a tight insertion of the scope through the splint.

In use during a colonoscopy, the colonoscope is inserted into the colon until further progress becomes difficult, at which time the tip of the colonoscope is typically located in the upper descending colon or the transverse colon. Using the colonoscope itself, the sigmoid loop is initially straightened. The splint, which was placed over the proximal shaft of the colonoscope prior to beginning the examination, is gently pushed into the colon over the scope with the aid of lubricants, such as "JOHNSON & JOHNSON K-Y JELLY"(a registered trademark of Johnson & Johnson). With full insertion of the splint, the proximal end of the splint remains outside the anus, while the distal end is in the descending colon. The placement of the splint allows and maintains an almost straight-line passage from the anus to the descending colon. The colonoscope is then advanced while the splint is held stationary. The splint keeps the sigmoid in a straightened position, prevents a loop from reforming and facilitates advancement of the scope to the cecum.

Despite its advantages, the prior art splint is very rarely utilized due to the risk of perforation of the colon by the splint. Perforations are caused by the entrapment of a piece of colonic wall between the distal end of the splint and the endoscope when the splint is moved inside the patient's colon. The entrapment can occur either when the splint is advanced over the scope or when the scope is withdrawn through the splint. Once entrapped, a piece of colonic wall can be sheared off by the relatively sharp edge of the distal end of the splint. If the entrapped piece of colonic lining includes all layers of the colonic wall, then it becomes a through and through perforation.

In the prior art devices, the space between the scope and the splint, approximately 2 millimeter in radius, has to exist to allow smooth movement of the scope and the splint against each other. Without this space, i.e., by modifying the prior art splint to have a very tight fit for the scope, two undesirable features would occur: 1) too much friction would occur between the scope and the splint, causing resistance to manipulations; and 2) damage to the scope as the splint rubs against the surface of the scope. In the invention which is the subject of the present patent, the space between the scope and the distal end of the splint is eliminated and the problems of friction to the movement of the endoscope against the splint, and its potential damage to the scope, are avoided.

U.S. Pat. No. 5,337,733 describes a tubular inserting device with variable rigidity. This long overtube is made of two thin walls with space between. The outer wall is made of semi-rigid, non-expandable material, while the inner wall is made of material which is radially deformable, allowing expansion and resolution of the intervening space. Fluid is injected into the proximal end of the overtube to expand the space. When the space is expanded, the two walls separate from each other creating a flexible overtube. Suctioning out the injected fluid removes the space, bringing the two walls into contact with each other. The external surface of the inner wall and the internal surface of the outer wall are lined with a cogwheel like arrangement that engage and lock against each other when the space between them is removed, thereby producing a rigid overtube. When the space is expanded by injecting fluid, the two walls separate and the overtube returns to its flexible state.

This prior art overtube is introduced over the endoscope. During the colonoscopy procedure, when flexibility of the overtube is desired, the space between the two walls is expanded. When rigidity of the overtube is desired, this space is eliminated. The invention described by U.S. Pat. No. 5,337,733 does not address the issue of the space between the distal edge of the splint and the scope. The present invention is much shorter, consists of only one wall and aims to address the problem of the space between the distal edge of the splint and the colonoscope.

Another invention, U.S. Pat. No. 4,601,283, describes the use of a wire made of memory shape alloy. This wire is inserted into the biopsy channel of the scope. By keeping the wire at certain temperatures, it returns and remains in its "memorized" straight shape, keeping the endoscope in a straightened position. The present invention avoids the necessity of the special wire and avoids the resultant possible damage to the biopsy channel, which has been reported to occur.

SUMMARY OF THE INVENTION

The sigmoid splint or overtube in accordance with the present invention solves the problems associated with the prior art devices described above. That is to say, the present invention provides a sigmoid splint or overtube that is effective in straightening the sigmoid during an endoscopic procedure to allow easy insertion of the scope while avoiding damage to the colon.

The sigmoid splint of the present invention is of tubular shape and made of a flexible but somewhat rigid material such as plastic, polyethylene or polyurethane, or other similar materials. Typically, the length of the splint will be 30 to 80 centimeters. Its distal end has an inner diameter of approximately 4 millimeters greater than the outside diameter of the scope. The proximal end of the splint has an outside diameter larger than the outside diameter of the distal end in order to prevent complete entry of the splint into a patient's body. The proximal end has a seal with a hole slightly larger than the scope to guide the scope through the splint and prevent loss of fluids.

The inner surface of the distal end of the splint has a seal made of an elastic, malleable, smooth, absorbent, soft and expandable material. Examples of such materials include sponge and foam rubber. The thickness of the distal seal is slightly greater than the gap between the scope and the splint, such that when the scope is passed through it, a tight fit is produced. The seal can protrude beyond the distal end of the splint. In the preferred embodiment, the portion extending beyond the splint has a tapered, streamlined configuration, producing a tapered end for the splint to facilitate its insertion into the colon. The more proximal portion of the seal is fastened or glued to the inner surface of the distal portion of the splint. The length of this seal can be from 1 centimeter, or less, to the entire length of the splint. That is, the distal seal itself may have the configuration of a hollow cylinder. To ease insertion of the scope, which has a blunt end, into the splint, the proximal end of the seal can also be tapered.

The distal seal should be well lubricated. A preferred lubricant is a hydrophilic substance, similar to that used to line glide-type guide wires, for example, the "TERUMO"(a registered trademark of Terumo Corporation) guide wire. These hydrophilic substances have the unique property of becoming extremely slippery when wet with water or saline. An adequate layer of the hydrophilic substance should be coated and/or impregnated into the distal seal. Water or saline that is applied to this seal will be retained and the sliding surface will be extremely slippery, allowing easy passage of the scope past the distal seal. The design of the present invention closes the potentially hazardous gap between the distal end of the splint and the scope and prevents undue friction, thereby allowing safe, easy and damage-free movement of the scope.

An injection port can be located at or near the proximal end of the splint for fitting a syringe. This port allows the injection of water or lubricant into the splint during an endoscopy, in order to periodically add wetness and lubrication to the surface of the distal and proximal seals. It also allows the injection of air to expand the colon to further ease insertion of the splint.

Small longitudinal grooves can be made on the inner surface of the distal seal to allow air that has been injected or infused into the splint through the injection port to exit from the distal end of the splint. These grooves can cut through the entire thickness of the seal, structuring the seal in a non-continuous fashion. The injection of air expands the colon ahead of where the splint is being inserted, thus further assuring that the colonic wall will not become entrapped by the distal end of the splint. Injected water or saline can also exit via these grooves, so that any potentially adherent colonic wall, or fecal material remaining in the colon, can be constantly pushed off from the distal end of the splint.

A bullet-tip device can be fitted over the end of the scope at the time of inserting the scope through the splint, before the scope is introduced into the patient to further facilitate insertion of the scope through the splint. Once the scope tip comes out of the seal, this bullet device is removed, and the scope/splint combination is ready for insertion into the patient's body. In cases where the scope needs to be removed and then reintroduced into the patient, such as removal of multiple polyps from the proximal colon, the splint may remain in the colon while the scope is removed. In these instances, the scope can be reintroduced into the splint by inserting a balloon catheter into the scope. The balloon is inflated once it exits the scope. By configuring the balloon in the shape of a bullet, the scope is similarly introduced through the splint inside the patient's colon. Once the tip of the scope exits the distal end of the splint, the balloon is deflated and removed from the scope.

Aside from applications in colonoscopy, the splint or overtube of the present invention can be applicable to other medical or non-medical procedures. The device of the present invention may also have useful applications in the upper gastrointestinal tract or other parts of the human anatomy.

Accordingly, the primary objective of the present invention is to provide a safe, effective and relatively easy to use device for facilitating the insertion and use of an endoscope during an endoscopy procedure.

It is also an important objective of the present invention to provide a sigmoid splint or overtube suitable for straightening and maintaining the straightness of the sigmoid colon during endoscopy.

Another important objective of the present invention is to provide a sigmoid splint or overtube having a tubular design with a tapered elongated seal at its distal end to seal the annular area around the endoscope and ease entry into the colon and a seal at its proximal end to prevent loss of fluids and to guide the endoscope through the splint.

Yet another important objective of the present invention is to provide a sigmoid splint or overtube having an injection port suitable for injecting fluids to lubricate the device so as to ease insertion or air to expand the area of the colon ahead of the device.

BRIEF DESCRIPTION OF THE DRAWINGS

In the drawings which illustrate the best modes presently contemplated for carrying out the present invention:

FIG. 5A through 5D shows use of the splint during a colonoscopy procedure; and

DETAILED DESCRIPTION OF THE PREFERRED EMBODIMENTS

Figure 1:
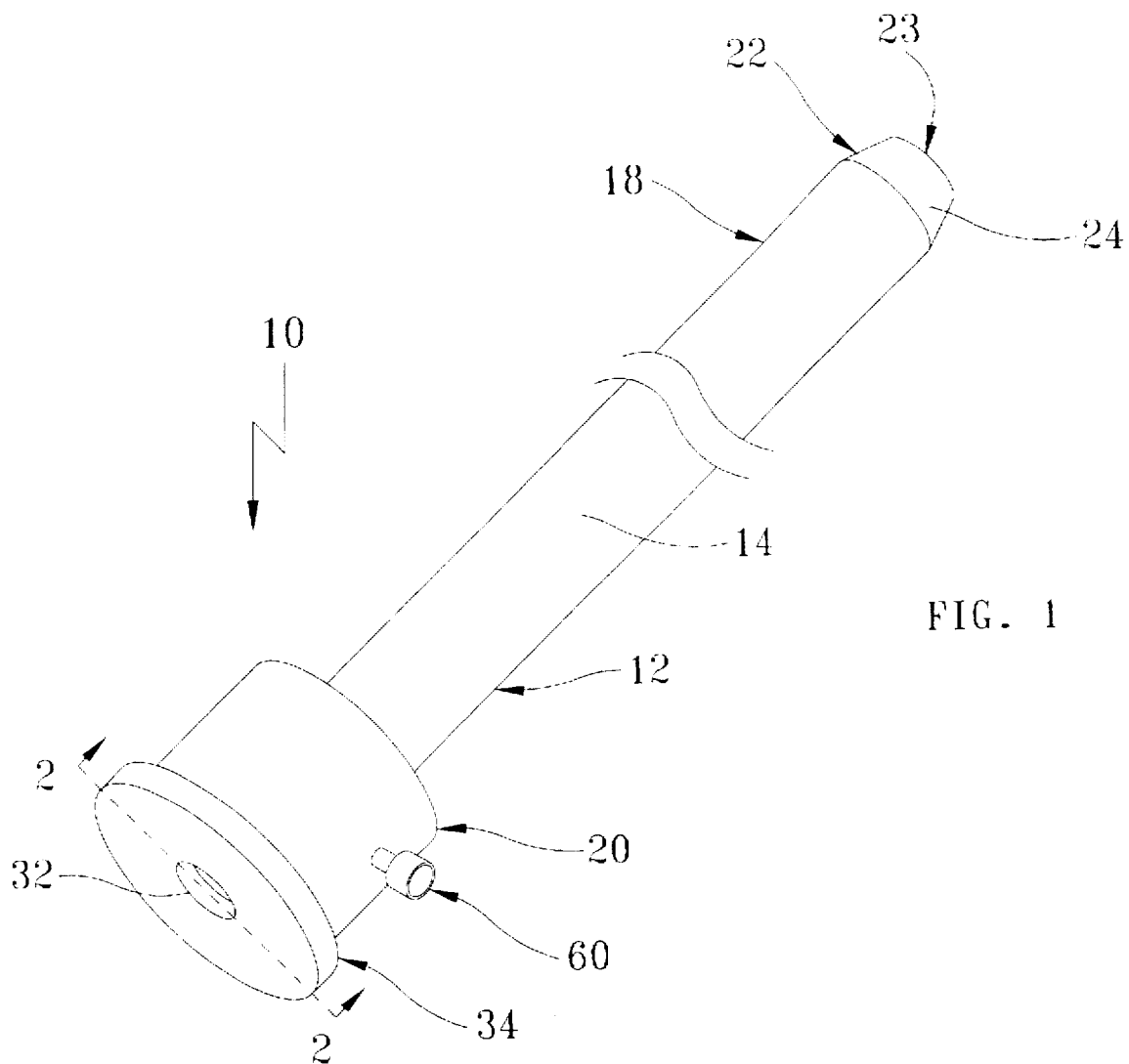
FIG. 1 is a perspective view of the sigmoid splint device that is the subject of this patent.

With reference to the figures where like elements have been given like numerical designations to facilitate understanding the present invention, and particularly with reference to the embodiments of the present invention illustrated in FIGS. 1 through 6, the sigmoid splint device is designated generally 10. The sigmoid splint 10 includes an elongated tubular member 12 with an outer surface 14 and an inner surface 16. The tubular member 12 has opposing ends, a distal end 18 which enters the human body and a proximal end 20 which has an outside diameter larger than the outside diameter of the distal end 18 to prevent complete entry into the human body during the procedures described herein. The inside diameter of tubular member 12 must be greater than the outside diameter of the endoscope to be used with the splint 10.

Figure 2:
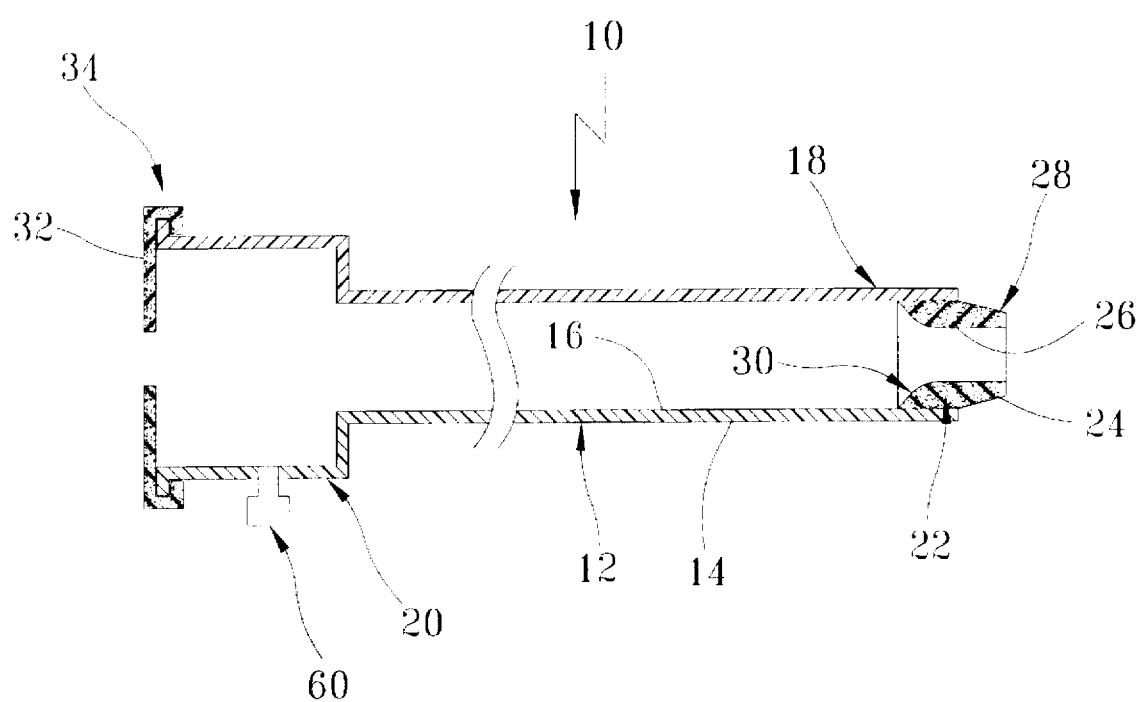
FIG. 2 is a cross-sectional view of the device in FIG. 1, showing the proximal end cap and an elongated and tapered distal seal.

Located at or near the distal end 18 of tubular member 12 is distal seal 22 having an opening 23, an external surface 24 and an internal surface 26. The external surface 24 of distal seal 22 attaches to inner surface 16 of tubular member 12. In the preferred embodiment, as shown in FIGS. 1 and 2, the distal seal 22 is elongated and extends beyond distal end 18 of tubular member 12. As also shown in FIGS. 1 and 2, the preferred embodiment utilizes distal seal 22 having both ends tapered. The forward taper 28 extending beyond the distal end 18 facilitates insertion of the splint 10 into the colon and further prevents undesirable capture of the colonic wall between the splint and the endoscope. The rearward taper 30 facilitates passage of the endoscope through the splint 10.

Located at or near the proximal end 20 of tubular member 12 is proximal seal 32 to seal the space between the inner surface 16 and the outside diameter of the endoscope. The use of proximal seal 32 guides the endoscope through the splint 10 and prevents loss of fluid from inside the splint 10. As shown in FIGS. 1 and 2, proximal seal 32 can be incorporated into an end cap 34 that attaches to the proximal end 20 of tubular member 12. The end cap 34 and proximal seal 32 can be a single-piece rubber diaphragm that removably attaches to proximal end 20.

Figure 3:
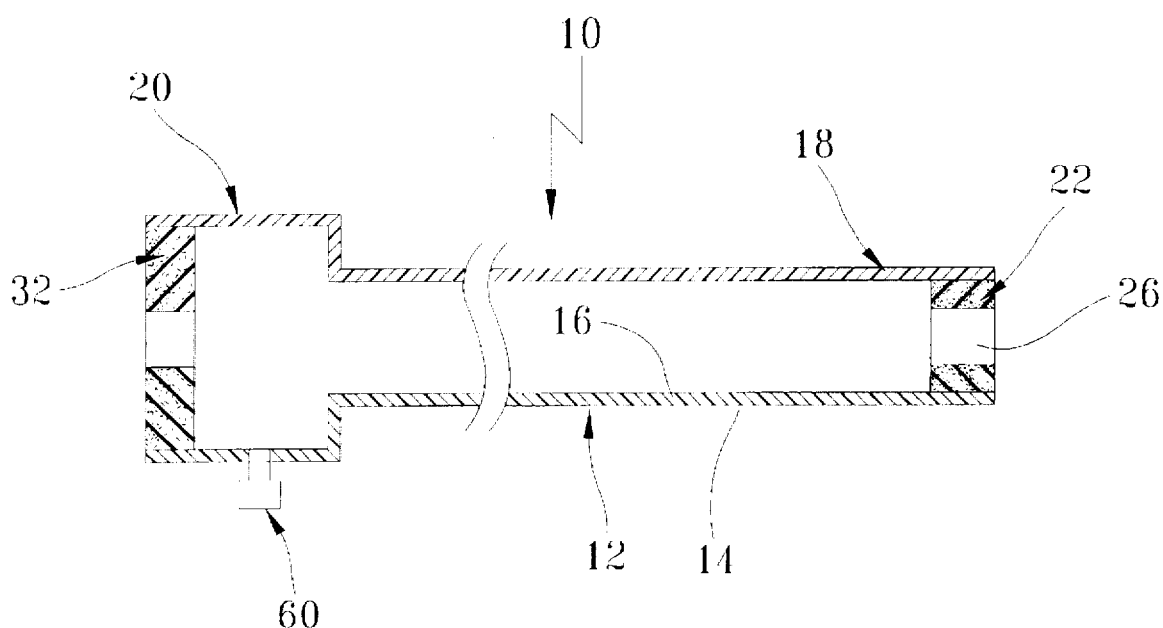
FIG. 3 is a cross-sectional view of the embodiment with ring-like sealing structures at both the distal and proximal ends of the splint.

As shown in FIG. 3, the distal seal 22 can be ring-like in configuration, i.e., not tapered, and located entirely inside the distal end 18 of tubular member 22. Even in this configuration, when the endoscope is inside the sigmoid splint 10, the distal seal 22 seals the annular space around the endoscope to prevent loss of fluid from inside tubular member 12 and to prevent the colonic wall from being trapped between the endoscope and the sigmoid splint 10. As also shown in FIG. 3, proximal seal 32 can also be ring-like and be located entirely within proximal end 20 of tubular member 12 to guide the endoscope and prevent loss of fluids out tubular member 12.

Figure 4A:
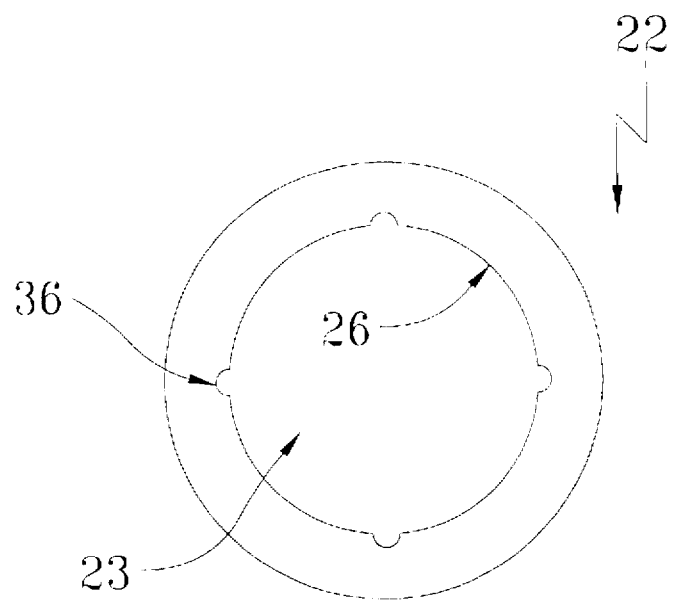
FIG. 4A is a cross-sectional view of the distal seal with longitudinal grooves cut into the distal seal.
Figure 4B:
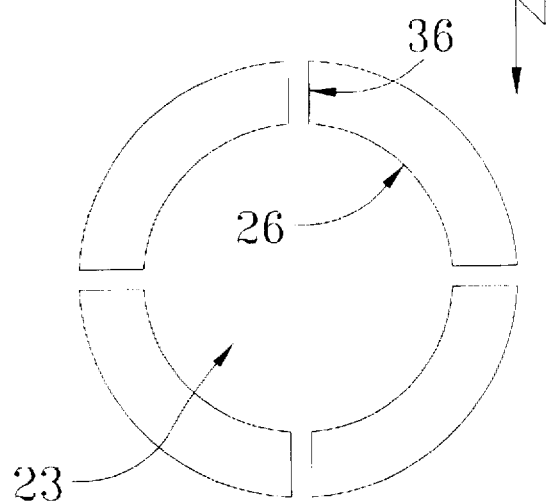
FIG. 4B is a cross-sectional view of the distal seal with longitudinal grooves cut entirely through the distal seal.

FIGS. 4A and 4B show the use of longitudinal grooves 36 in distal seal 22 to allow the passage of fluid around distal seal 22 when the endoscope is inside splint 10. FIG. 4A shows longitudinal grooves 36 only partially cut into distal seal 22. FIG. 4B shows longitudinal grooves 36 cut entirely through distal seal 22. In either configuration, longitudinal grooves 36 would extend over the entire length of distal seal 22. The ability to pass fluids around distal seal 22 allows the introduction of wetting fluids into tubular member 12 to ensure distal seal 22 is sufficiently moist to facilitate smooth movement of the endoscope. Longitudinal grooves 36 also permit the introduction of fluid into and through tubular member 12 to expand the colon in front of the endoscope and to clear unwanted colonic wall or fecal matter from the distal end 18 of tubular member 12. Alternatively, distal seal 22 can incorporate one or more openings within the body of the seal 22 to allow fluid to pass through distal seal 22 and accomplish the objectives set forth above.

Figure 5B:
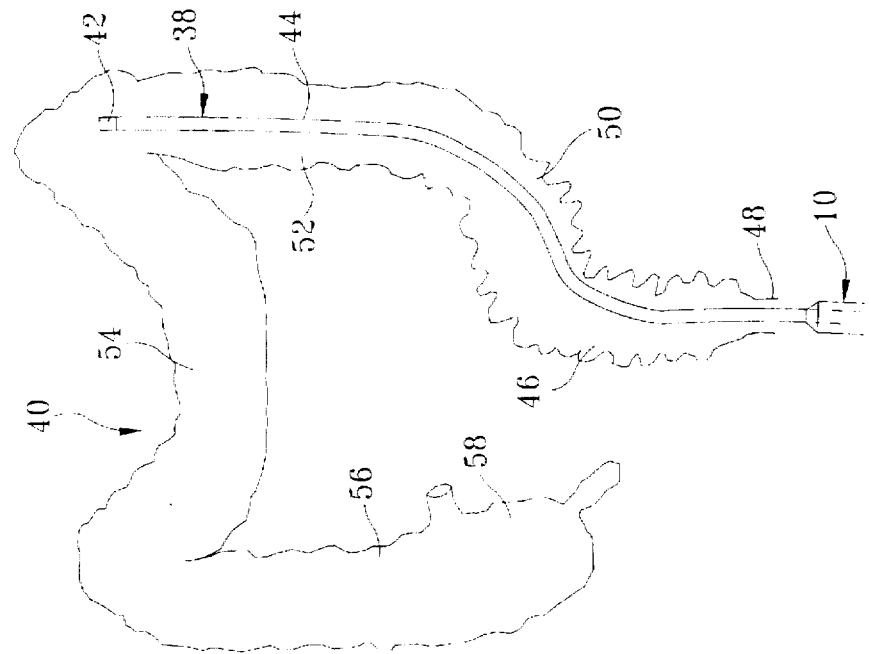
Figure 5A:
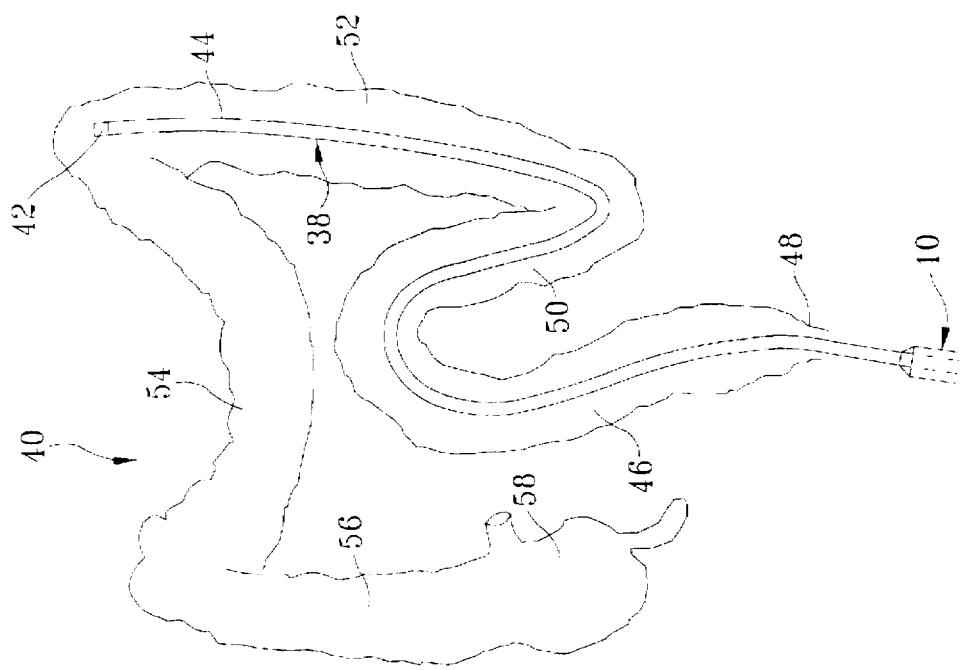

In use during a colonoscopy, as shown in FIGS. 5A through 5D, the colonoscope 38 is initially inserted or preloaded into the splint 10 prior to beginning the procedure to investigate the colon 40. The tip 42 and body 44 of endoscope 38 is introduced into the rectum 46 through the anus 48 and then into the sigmoid colon 50. After negotiating the loop in the sigmoid colon 50, the endoscope 38 enters the descending colon 52. Further advancement of the tip 42 is made easier by partially withdrawing the endoscope 38 to straighten the sigmoid colon 50 with the body 44 of endoscope 38 (as shown in FIG. 5B). Once the sigmoid colon 50 is straightened, the distal end 18 of tubular member 12 is slid over endoscope 38 and through the anus 48 and into the rectum 46, the sigmoid colon 50 and then the descending colon 52 (as shown in FIG. 5C). The proximal end 20 of tubular member 12 remains outside the anus 48. The presence of the splint 10 inside the sigmoid colon 50 and descending colon 52 prevents reformation of the loop, thereby facilitating further insertion of the endoscope 38 through the transverse colon 54 and ascending colon 56 and then into the cecum 58 (as shown in FIG. 5D). After completing the procedure, the endoscope 38 and splint 10 are removed from the patient.

As shown in FIG. 3, an injection port 60 located at or near proximal end 20 of tubular member 12 allows the introduction of fluids, such as water or lubricants into the splint 10 to wet distal seal 22 and proximal seal 32 to ensure that they remain in a pliable and slippery condition. Injection port 60 also allows the injection of fluid through tubular member 12 and into colon 40 to expand colon 40, further easing insertion of splint 10, and to clear a path through colon 40 for tubular member 12. Injection port 60 should be suitable for fitting a syringe.

Figure 6:
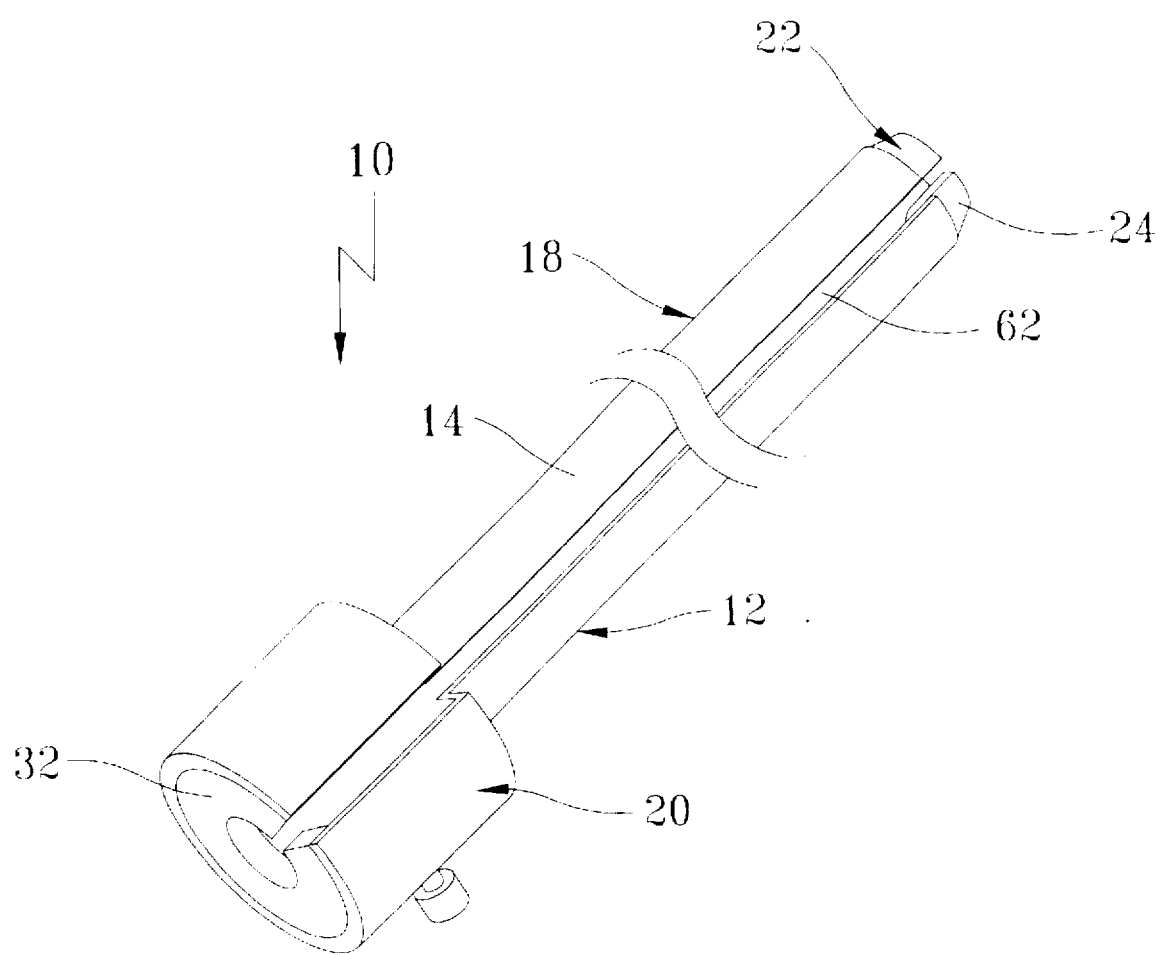
FIG. 6 shows a tubular member with a longitudinally oriented open-ended slot.

Another embodiment of the present invention, shown in FIG. 6, utilizes a longitudinally oriented open-ended slot 62 on tubular member 12. The slot is sized to removably receive endoscope 38. With this embodiment, the endoscope 38 does not have to be inserted or pre-loaded onto sigmoid splint 10 prior to inserting scope 38 into the patient, thereby allowing the full length of scope 38 to be utilized for manipulations. After the scope is introduced into the descending colon 52 or transverse colon 54, it is straightened in the usual fashion by reducing the sigmoid loop. The splint 10 is then loaded onto the scope 38 by opening the slot 62. After loading, the slot can be closed by sealing it with adhesive tape or by utilizing a locking mechanism either on or in tubular member 12. The other components of this embodiment, other than slot 62, are identical to the embodiments described above and it is used during an endoscopy examination as set forth above.

While there is shown and described herein certain specific alternative forms of the invention, it will be readily apparent to those skilled in the art that the invention is not so limited, but is susceptible to various modifications and rearrangements in design and materials without departing from the spirit and scope of the invention. In particular, it should be noted that the present invention is subject to modification with regard to the dimensional relationships set forth herein and modifications in assembly, materials, size, shape, and use.

What is claimed is:

1. A splint device for use in medical endoscopy to guide an endoscope having an outer diameter, comprising:

an elongated tubular member having an outer surface, an inner surface, a distal end and a proximal end, said distal end having a first outside diameter and said proximal end having a second outside diameter, said second outside diameter being greater than said first outside diameter;

first sealing means located at said distal end for sealing the annular space between said inner surface of said distal end and the endoscope when the endoscope is inside said tubular member, said first sealing means having an opening and an internal surface, said opening having a diameter slightly smaller than or substantially equal to the outer diameter of the endoscope; and second sealing means located at said proximal end for sealing the annular space between said inner surface of said proximal end and the endoscope when the endoscope is inside said tubular member.

2. The splint device according to claim 1, wherein said tubular member is semi-rigid.

3. The splint device according to claim 1, wherein said tubular member further comprises a longitudinally oriented open-ended slot for removably receiving the endoscope and closure means for closing said slot when the endoscope is in said tubular member.

4. The splint device according to claim 1, wherein said first sealing means is absorbent.

5. The splint device according to claim 1, wherein said first sealing means is coated or impregnated with a lubricant.

6. The splint device according to claim 5, wherein said lubricant is a hydrophilic substance.

7. The splint device according to claim 1, wherein said first sealing means further comprises passage means for allowing fluid to pass through said distal end of said tubular member when the endoscope is engaged in the splint.

8. The splint device according to claim 1, wherein said passage means is one or more small longitudinal grooves on said first sealing means.

9. The splint device according to claim 1, wherein said first sealing means is elongated.

10. The splint device according to claim 1, wherein said first sealing means extends beyond said distal end of said tubular member.

11. The splint device according to claim 1, wherein said first sealing means has one or more tapered ends.

12. The splint device according to claim 1, wherein said second sealing means has an opening, said opening having an inside diameter slightly smaller than or substantially equal to the outside diameter of the endoscope.

13. The splint device according to claim 1, wherein said second sealing means is contained within an end cap removably connected to said proximal end of said tubular member.

14. The splint device according to claim 1 which further comprises injection means located between said first and second sealing means near said proximal end of said tubular member for injecting fluid into the annular space between said inner surface of said tubular member and the endoscope.

15. The splint device according to claim 14, wherein said injection means is suitable for injecting fluids with a syringe.

16. The splint device according to claim 1, wherein said first sealing means is compressible.

17. A splint device for use in medical endoscopy to guide an endoscope having an outer diameter, comprising:

a semi-rigid elongated tubular member having an outer surface, an inner surface, a distal end and a proximal end, said distal end having a first outside diameter and said proximal end having a second outside diameter, said second outside diameter being greater than said first outside diameter;

first sealing means located at said distal end for sealing the annular space between said inner surface and the endoscope when the endoscope is inside said tubular member, said first sealing means having an opening, said opening having a diameter slightly smaller than or substantially equal to the outer diameter of the endoscope, said first sealing means having passage means for allowing fluid to pass through said distal end of said tubular member when the endoscope is engaged in the splint, said first sealing means being coated or impregnated with a lubricant;

second sealing means located at said proximal end for sealing the annular space between said inner surface of said proximal end and the endoscope when the endoscope is inside said tubular member; and injection means at said proximal end of said tubular member for injecting fluid into said tubular member between said first sealing means and said second sealing means when the endoscope is engaged in the splint, said injection means in fluid communication with the annular space between said inner surface of said tubular member and the endoscope.

18. The splint device according to claim 17, wherein said first sealing means is substantially absorbent.

19. The splint device according to claim 17, wherein said lubricant is a hydrophilic substance.

20. The splint device according to claim 17, wherein said passage means comprises one or more small longitudinal grooves.

21. The splint device according to claim 17, wherein said injection means is suitable for injecting fluids with a syringe.

22. A method of using a sigmoid splint having a tight-fitting distal seal to help introduce an endoscope through the sigmoid colon into the proximal colon to perform a medical procedure, comprising the steps of:

(a) lubricating the endoscope with a lubricant;

(b) introducing the endoscope into the rectum through the anus and then beyond the sigmoid colon having a sigmoid loop;

(c) partially withdrawing the endoscope so as to straighten the sigmoid colon with the endoscope;

(d) lubricating the distal seal and the outside surface of the splint with a lubricant;

(e) inserting the splint over the endoscope through the anus into the rectum, sigmoid colon and descending colon to prevent reformation of the sigmoid loop;

(f) advancing the endoscope through the proximal colon to the cecum;

(g) performing the desired medical procedure;

(h) withdrawing the endoscope from the colon with the splint held in place;

(i) withdrawing the splint through the anus; and (j) withdrawing the endoscope through the anus.

23. The method of using a sigmoid splint to introduce a medical instrument through the sigmoid loop recited in claim 22 further comprising the steps of connecting a supply of aqueous-based solution to the splint prior to insertion of the splint into the anus, injecting said aqueous-based solution into the annular space between the splint and the endoscope after insertion of the splint into the colon, periodically injecting said aqueous solution into the splint while advancing the endoscope to the cecum, and periodically injecting said aqueous solution into the splint while withdrawing the endoscope from the colon.

24. The method of using a sigmoid splint to introduce a medical instrument through the sigmoid colon recited in claim 22 further comprising the step of placing the splint over the endoscope prior to introducing the splint into the rectum.

25. The method of using a sigmoid splint to introduce a medical instrument through the sigmoid colon recited in claim 22 further comprising the steps of placing the endoscope in the splint through a slot in the splint after straightening the sigmoid colon with the endoscope and closing said slot after the endoscope is in the splint.

26. The method of using a sigmoid splint to introduce a medical instrument through the sigmoid colon recited in claim 25 further comprising the step of sealing said slot with an adhesive tape after closing said slot.

* * * * *